United States Patent
Iimura et al.

(10) Patent No.: US 7,091,218 B1
(45) Date of Patent: Aug. 15, 2006

(54) 4-SUBSTITUTED PIPERIDINE COMPOUND

(75) Inventors: Yoichi Iimura, Ibaraki (JP); Takashi Kosasa, Ibaraki (JP)

(73) Assignee: Eisai Co., Ltd., Tokyo (JP)

( * ) Notice: Subject to any disclaimer, the term of this patent is extended or adjusted under 35 U.S.C. 154(b) by 537 days.

(21) Appl. No.: 10/069,073

(22) PCT Filed: Sep. 1, 2000

(86) PCT No.: PCT/JP00/05968

§ 371 (c)(1),
(2), (4) Date: Feb. 21, 2002

(87) PCT Pub. No.: WO01/16105

PCT Pub. Date: Mar. 8, 2001

(30) Foreign Application Priority Data

Sep. 1, 1999 (JP) .................................. 11-247115

(51) Int. Cl.
*A61P 25/28* (2006.01)
*A61K 31/445* (2006.01)
*A61K 31/55* (2006.01)
*C07D 211/32* (2006.01)
*C07D 401/06* (2006.01)

(52) U.S. Cl. ...................................... 514/319; 546/206
(58) Field of Classification Search ................ 514/319; 546/206

See application file for complete search history.

(56) References Cited

U.S. PATENT DOCUMENTS

| 5,100,901 A | 3/1992 | Sugimoto et al. ........... 514/319 |
| 5,750,542 A | 5/1998 | Villabos et al. ............. 514/322 |
| 6,277,866 B1 | 8/2001 | Takeuchi et al. ............ 514/319 |
| 6,677,330 B1 | 1/2004 | Iimura et al. .............. 514/18.3 |
| 2002/0177593 A1 | 11/2002 | Ishihara et al. .......... 514/227.5 |
| 2004/0048893 A1* | 3/2004 | Lerman et al. ............. 514/319 |

FOREIGN PATENT DOCUMENTS

| EP | 0 602 242 A1 | 6/1994 |
| JP | 9-268176 A | 10/1997 |
| JP | 2000-319257 | 11/2000 |
| WO | WO 92/17475 A1 | 10/1992 |
| WO | WO 00/18391 A1 | 4/2000 |
| WO | 00/51985 A1 | 9/2000 |
| WO | WO 00/57880 A1 | 10/2000 |
| WO | WO 02/02526 A1 | 1/2002 |

OTHER PUBLICATIONS

CAPLUS printout of U.S. 2004/0048893, Mar. 2004.*
Antony C. Wilbraham et al.; Introduction to Organic and Biological Chemistry; Scientific Library, Feb. 5, 1985, Patent & Trademark Office, pp. 268-269.

* cited by examiner

*Primary Examiner*—Brenda Coleman
(74) *Attorney, Agent, or Firm*—Birch, Stewart, Kolasch and Birch, LLP

(57) ABSTRACT

The present invention provides a novel compound having an excellent acetylcholinesterase inhibitory effect. That is, it provides a compound represented by formula:

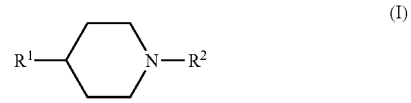

(I)

(wherein $R^1$ and $R^2$ represent substituents), a pharmacologically acceptable salt thereof or hydrates thereof.

14 Claims, No Drawings

4-SUBSTITUTED PIPERIDINE COMPOUND

This application is the national phase under 35 U.S.C. § 371 of PCT International Application No. PCT/JP00/05968 which has an International filing date of Sep. 1, 2000, which designated the United States of America.

FIELD OF THE INVENTION

The present invention relates to a novel compound useful as an acetylcholinesterase inhibitor, a salt thereof and hydrates thereof, and to a process for producing them.

PRIOR ART

It is known that senile dementia such as Alzheimer-type senile dementia, cerebrovascular dementia, attention deficit hyperactivity disorder etc. are accompanied with cholinergic hypofunction. Currently, acetylcholinesterase inhibitors have been acknowledged to be useful as a remedy for these diseases and actually used in clinical applications. For example, as their typical remedies, there have been known donepezil hydrochloride (1-benzyl-4-[(5,6-dimethoxy-1-indanon)-2-yl]methylpiperidine hydrochloride), and also rivastigmine (3-[1-(dimethylamino)ethyl]phenyl N-ethyl-N-methylcarbamate), metrifonate (dimethyl (2,2,2-trichloro-1-hydroxyethyl)phosphate), tacrine hydrochloride (1,2,3,4-tetrahydro-9-acridinamine), galanthamine hydrobromide, neostigmine, physostigmine etc.

However, among the aforementioned medicaments, it is only donepezil hydrochloride that has been acknowledged sufficient usefulness in consideration of pharmacological activity, side effect, number of administrations, form of administration etc., and short of it no acetylcholineesterase inhibitor that is clinically useful has been found yet. Although donepezil hydrochloride is an excellent medicine, it has been keenly desired to provide besides donepezil hydrochloride an acetylcholineesterase inhibitor that has excellent effect and is highly useful since an acetylcholineesterase inhibitor that exhibits more excellent effect, if available, will offer a wider choice of options in selecting medicines in clinical fields.

DISCLOSURE OF THE INVENTION

Under these circumstances, the present inventors have made intensive research over the years in order to develop medicines having more excellent effects and higher safety. As a result, they have succeeded in synthesizing a novel compound represented by the formula:

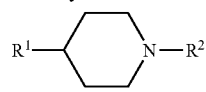
(I)

wherein, $R^1$ represents any group selected from the groups represented by formulae:

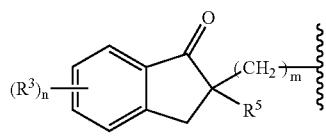

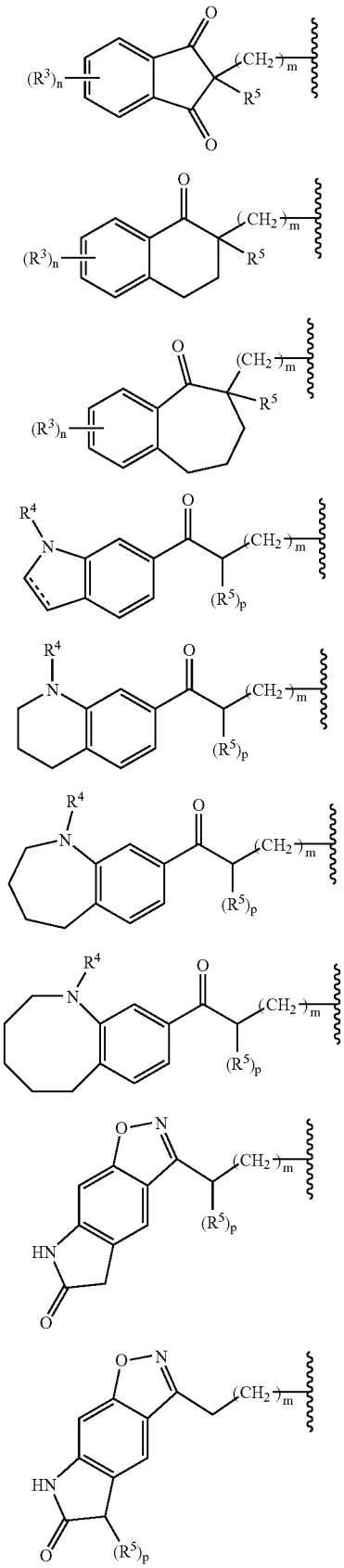

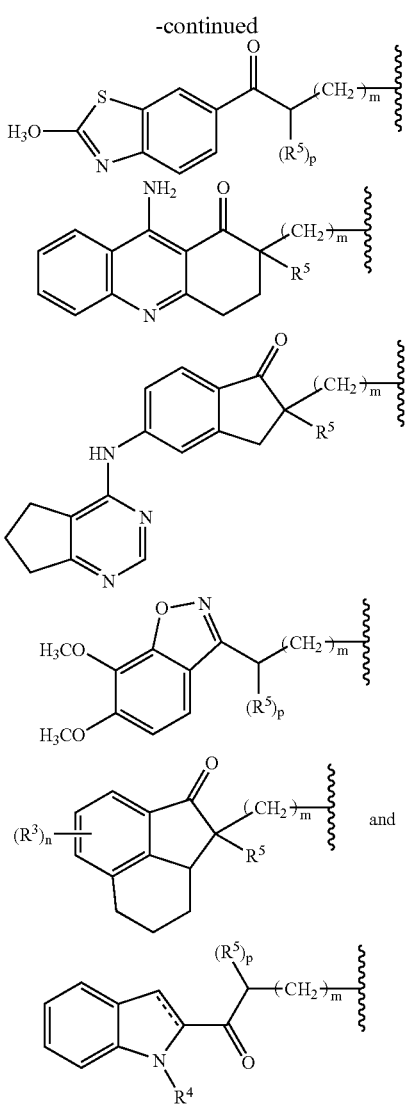

(wherein (R³)s are the same as or different from each other and each represents hydrogen atom, a halogen atom, hydroxyl group, a $C_{1-6}$ alkyl group, a $C_{3-8}$ cycloalkyl group, a $C_{1-6}$ alkoxy group, a $C_{1-6}$ alkoxyalkoxy group, a halogeno $C_{1-6}$ alkyl group, a hydroxy $C_{1-6}$ alkyl group, a cyano $C_{1-6}$ alkyl group, an amino $C_{1-6}$ alkyl group, a halogeno $C_{1-6}$ alkoxy group, a hydroxy $C_{1-6}$ alkoxy group, a cyano $C_{1-6}$ alkoxy group, a lower acyl group, nitro group, an optionally substituted amino group, an optionally substituted carbamoyl group, mercapto group or a $C_{1-6}$ thioalkoxy group; $R^4$ represents hydrogen atom or a $C_{1-6}$ alkyl group; $R^5$ represents a halogen atom (provided that fluorine is excluded), hydroxy group, a $C_{1-6}$ alkyl group, a $C_{1-6}$ alkoxy group, cyano group, a halogeno $C_{1-6}$ alkyl group, a hydroxy $C_{1-6}$ alkyl group, a cyano $C_{1-6}$ alkyl group, an amino $C_{1-6}$ alkyl group, nitro group, an azido group, an optionally substituted amino group, an optionally substituted carbamoyl group, an optionally substituted carboxyl group, mercapto group or a $C_{1-6}$ thioalkoxy group; the partial structure --- represents a single bond or double bond; m is 0 or an integer from 1 to 6; n is an integer from 1 to 4; and p is an integer of 1 or 2); and $R^2$ represents a $C_{3-8}$ cycloalkylmethyl, a 2,2-(alkylenedioxy)ethyl or a group represented by the formula:

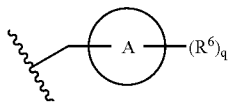

wherein the ring A represents a benzene ring or a heterocyclic ring; $(R^6)$s are the same as or different from each other and each represents hydrogen, a halogen atom, hydroxyl group, nitrile group, a $C_{1-6}$ alkyl group, a $C_{3-8}$ cycloalkyl group, a $C_{1-6}$ alkoxy group, a $C_{1-6}$ alkoxyalkoxy group, an aryloxy group, an aralkyloxy group, a halogeno $C_{1-6}$ alkyl group, a hydroxy $C_{1-6}$ alkyl group, a cyano $C_{1-6}$ alkyl group, a halogeno $C_{1-6}$ alkoxy group, a hydroxy $C_{1-6}$ alkoxy group, a cyano $C_{1-6}$ alkoxy group, a lower acyl group, nitro group, an optionally substituted amino group, an optionally substituted amide group, mercapto group or a $C_{1-6}$ thioalkoxy group, and two of the $R^6$ may together form an aliphatic ring, an aromatic ring, a heterocyclic ring or an alkylenedioxy ring; and q is 0 or an integer from 1 to 5. Further, they have found that the compound represented by the above formula (I), a salt thereof and hydrates thereof exhibit an excellent acetylcholinesterase inhibitory effect and the intended objects have been attained therewith. Thus, they have achieved the present invention.

That is, the first feature of the present invention is:

(1) the compound represented by the above formula (I), a pharmacologically acceptable salt thereof or hydrates thereof, and further, (2) in the above (1), $R^1$ may be a group represented by the formula:

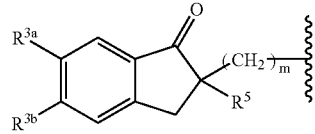

wherein $R^{3a}$ and $R^{3b}$ are the same as or different from each other and each represents a $C_{1-6}$ alkoxy group; and $R^5$ and m have the same meanings as defined above;

(3) in the above (2), $R^{3a}$ and $R^{3b}$ may be methoxy group;

(4) in the above (1) to (3), $R^5$ may be chlorine or bromine;

(5) in the above (1) to (4), m may be 1;

(6) in the above (1), $R^2$ may be a group represented by the formula:

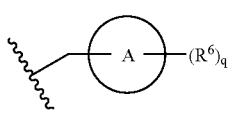

wherein the ring A, $R^6$ and q have the same meanings as defined above;

(7) in the above (6), the ring A may be a benzene ring;

(8) in the above (6), the ring A may be a pyridine ring;

(9) in the above (6), q may be an integer of 1 or 2; and

(10) in the above (1), the compound may be any compound selected from:
1-benzyl-4-[(5,6-dimethoxy-2-chloro-1-indanon)-1-yl]methylpiperidine,
1-benzyl-4-[(5,6-dimethoxy-2-bromo-1-indanon)-2-yl]methylpiperidine,
1-benzyl-4-[(5,6-dimethoxy-2-iodo-1-indanon)-2-yl]methylpiperidine,
1-benzyl-4-[(5,6-dimethoxy-2-hydroxy-1-indanon)-2-yl]methylpiperidine,
1-benzyl-4-[(5,6-dimethoxy-2-methyl-1-indanon)-2-yl]methylpiperidine,
1-benzyl-4-[(5,6-dimethoxy-2-ethyl-1-indanon)-2-yl]methylpiperidine,
1-benzyl-4-[(5,6-dimethoxy-2-azido-1-indanon)-2-yl]methylpiperidine,
1-benzyl-4-[(5,6-dimethoxy-2-amino-1-indanon)-2-yl]methylpiperidine,
1-benzyl-4-[(5,6-dimethoxy-2-methylamino-1-indanon)-2-yl]methylpiperidine,
1-benzyl-4-[(5,6-dimethoxy-2-dimethylamino-1-indanon)-2-yl]methylpiperidine,
1-benzyl-4-[(5,6-dimethoxy-2-acetamide-1-indanon)-2-yl]methylpiperidine,
1-benzyl-4-[(5,6-dimethoxy-2-methanesulfonamide-1-indanon)-2-yl]methylpiperidine,
3-(1-benzylpiperidin-4-yl)-2-chloro-1-(2,3,4,5-tetrahydro-1H-1-benzoazepin-8-yl)-1-propanone,
3-(1-benzylpiperidin-4-yl)-2,2-dichloro-1-(2,3,4,5-tetrahydro-1H-1-benzoazepin-8-yl)-1-propanone,
5,7-dihydro-3-[1-chloro-2-[(1-(phenylmethyl)-4-piperidinyl]ethyl]-6H-pyrrolo[4,5-f]-1,2-benzoisooxazol-6-one,
5,7-dihydro-3-(1,1-dichloro-2-[(1-(phenylmethyl)-4-piperidinyl]ethyl)-6H-pyrrolo[4,5-f]-1,2-benzoisooxazol-6-one,
1-(2-methyl-6-benzothiazolyl)-3-[1-(phenylmethyl)-4-piperidinyl]-2-chloro-1-propanone, and
1-(2-methyl-6-benzothiazolyl)-3-[1-(phenylmethyl)-4-piperidinyl]-2,2-dichloro-1-propanone.

The second feature of the present invention is:

(11) a medicament containing the compound described in the above (1), a salt thereof or hydrates thereof, and further,

(12) the medicament in the above (11) may be an acetylcholinesterase inhibitor;

(13) the medicament in the above (11) may be an agent for treating, preventing or ameliorating various types of senile dementia, cerebrovascular dementia or attention deficit hyperactivity disorder; and

(14) the senile dementia in the above (13) may be Alzheimer-type senile dementia.

The present invention provides a medical composition comprising a pharmacologically effective amount of the compound described in the above (1), a pharmacologically acceptable salt thereof or hydrates thereof, and a pharmacologically acceptable carrier.

Also, the present invention provides a method for preventing, treating or ameliorating diseases against which the inhibition of an acetylcholinesterase is effective and a method for treating, preventing or ameliorating various types of senile dementia, cerebrovascular dementia or attention deficit hyperactivity disorder, by administering a pharmacologically effective amount of the compound described in the above (1), a pharmacologically acceptable salt thereof or hydrates thereof to a patient.

Further, the present invention provides use of the compound described in the above (1), a pharmacologically acceptable salt thereof or hydrates thereof for producing an agent for preventing, treating or ameliorating diseases against which the inhibition of an acetylcholinesterase is effective, for producing an acetylcholineesterase inhibitor, and for producing an agent for preventing, treating or ameliorating various types of senile dementia, cerebrovascular dementia or attention deficit hyperactivity disorder.

Hereinafter, the symbols, terms, etc., used in the specification of the present application will be explained and the present invention will be illustrated in detail.

Note that the structural formula for a compound as used in the specification of the present application may be expressed as indicating a certain isomer or isotope for the sake of convenience. However, in the present invention, a compound represented by a structural formula is to be construed as including all the possible isomers such as geometric isomers, optical isomers due to asymmetric carbon atom, stereoisomers and tautomers and mixtures thereof as well as isotopes and should not be limited to what is expressed by the formula that is presented only for the convenience sake. The compound may be anyone of isomers or mixtures thereof, or any one of isotopes. Therefore, a compound may have an asymmetric carbon atom or atoms in the molecule and hence there may be optically active forms or racemic form. In the present invention compounds are not limited to particular ones but include both of them. Further, crystal polymorphism may exist and similarly the present invention is not limited to a particular crystal form but may include any one of crystal forms or mixtures thereof. The compounds of the present invention may be hydrates as well as anhydrides.

In the formula (I) above, the "halogen atom" represented by $R^3$ in the definition of $R^1$ indicates an atom such as fluorine, chlorine, bromine or iodine, preferably fluorine, chlorine or bromine. The "halogen atom" represented by $R^5$ includes halogen atoms other than fluorine and includes, for example, chlorine, bromine, iodine and the like, and preferably chlorine and bromine.

The "$C_{1-6}$ alkyl group" represented by $R^3$, $R^4$ and $R^5$ above means an alkyl group having 1 to 6 carbon atoms and includes linear or branched alkyl groups, for example, methyl group, ethyl group, n-propyl group, i-propyl group, n-butyl group, i-butyl group, t-butyl group, n-pentyl group, i-pentyl group, neopentyl group, hexyl group, 1-methylpropyl group, 1-methylbutyl group, 2-methylbutyl group etc.

The "$C_{3-8}$ cycloalkyl group" represented by $R^3$ above means a cyclic alkyl group having 3 to 8 carbon atoms and includes, for example, a cyclopropyl group, a cyclobutyl group, a cyclopentyl group, a cyclohexyl group, a cycloheptyl group, a cyclooctyl group etc.

The "$C_{1-6}$ alkoxy group" represented by $R^3$ and $R^5$ above means a group consisting of a group having the same meaning as the "$C_{1-6}$ alkyl group" defined above and an oxygen atom bonded thereto and includes linear or branched alkoxy groups, for example, methoxy group, ethoxy group, n-propoxy group, i-propoxy group, n-butoxy group, i-butoxy group, t-butoxy group, pentyloxy group, hexyloxy group etc.

The "$C_{1-6}$ alkoxyalkoxy group" represented by $R^3$ above means a group consisting of a group having the same meaning as the "$C_{1-6}$ alkoxy group" defined above and another "$C_{1-6}$ alkoxy group" bonded thereto and includes, for example, methoxymethoxy group, methoxyethoxy group, methoxypropoxy group, ethoxymethoxy group, ethoxyethoxy group, ethoxypropoxy group, propoxypropoxy group etc.

The "halogeno $C_{1-6}$ alkyl group" represented by $R^3$ and $R^5$ above means a group consisting of a group having the same meaning as the $C_{1-6}$ alkyl group defined above having one or more halogen atoms bonded thereto which may be the same as or different from and includes, for example, chloromethyl group, dichloromethyl group, trichloromethyl group, fluoromethyl group, difluoromethyl group, trifluoromethyl group, fluoromethyl group, difluoromethyl group, trifluoromethyl group etc.

The "hydroxy $C_{1-6}$ alkyl group" represented by $R^3$ and $R^5$ above means a group consisting of a group having the same meaning as the $C_{1-6}$ alkyl group defined above having one or more hydroxyl groups bonded thereto and includes, for example, hydroxymethyl group, hydroxyethyl group, 2,3-dihydroxypropyl group etc.

The "cyano $C_{1-6}$ alkyl group" represented by $R^3$ and $R^5$ above means a group consisting of a group having the same meaning as the $C_{1-6}$ alkyl group defined above having bonded thereto one or more cyano groups bonded thereto and includes, for example, cyanomethyl group, cyanoethyl group, cyanopropyl group etc.

The "halogeno $C_{1-6}$ alkoxy group" represented by $R^3$ above means the "halogeno $C_{1-6}$ alkyl group" having the same meaning as the halogeno $C_{1-6}$ alkyl group defined above, which is bonded to an oxygen atom, the "hydroxy $C_{1-6}$ alkoxy group" means the "hydroxy $C_{1-6}$ alkyl group" having the same meaning as the hydroxy $C_{1-6}$ alkyl group as defined above, which is bonded to an oxygen atom, and the "cyano $C_{1-6}$ alkoxy group" means the "cyano $C_{1-6}$ alkyl group" having the same meaning as the cyano $C_{1-6}$ alkyl group as defined above, which is bonded to an oxygen atom.

The "lower acyl group" represented by $R^3$ above means a linear or branched acyl group derived from a fatty acid having 1 to 6 carbon atoms and includes, for example, formyl group, acetyl group, propionyl group, butyryl group, isobutyryl group, valeryl group, isovaleryl group, pivaloyl group, hexanoyl group etc.

The "optionally substituted amino group" represented by $R^3$ and $R^5$ above means an amino group of which the nitrogen atom may be substituted by a group such as a $C_{1-6}$ alkyl group and further the amino group includes cyclic amino groups. The "optionally substituted amino group" includes, for example, amino group (—$NH_2$), methylamino group (—$NHCH_3$), dimethylamino group (—$N(CH_3)_2$), pyrrolidinyl group, pyrazolinyl group, piperidyl group, piperazinyl group etc.

The "optionally substituted carbamoyl group" represented by $R^3$ and $R^5$ above means an amide group of which the nitrogen atom may be substituted by a group such as a $C_{1-6}$ alkyl group and further the amide group includes amide groups of cyclic amine. The "optionally substituted amide group" includes, for example, amide group (—$CONH_2$), N-methylamide group (—$CONHCH_3$), N,N-dimethylamide group (—$CON(CH_3)_2$), N-ethylamide group (—$CONHC_2H_5$), N,N-diethylamide group (—$CON(C_2H_5)_2$), N-methyl-N-ethylamide group (—$CON(CH_3)(C_2H_5)$), pyrrolidinylcarbonyl group, pyrazolinylcarbonyl group, piperidylcarbonyl group, piperazinylcarbonyl group etc.

The "$C_{1-6}$ thioalkoxy group" represented by $R^3$ and $R^5$ above means a group consisting of a group having the same meaning as the $C_{1-6}$ alkyl group defined above bonded to a sulfur atom and includes, for example, methylthio group (—$SCH_3$), ethylthio group (—$SC_2H_5$) etc.

In the formula (I) above, the symbol m in $R^1$ indicates 0 or an integer from 1 to 6. m is preferably 0 or an integer from 1 to 5, more preferably 0 or an integer from 1 to 3, still more preferably 0 or an integer of 1 or 2 and most preferably 0 or 1. The symbol n indicates an integer of 1 to 4. n is preferably an integer from 1 to 3 and more preferably an integer of 1 or 2. Further, the symbol p indicates an integer of 1 or 2. p is preferably 1.

In the above formula (I), preferred groups represented by $R^1$ are those groups represented by the formula:

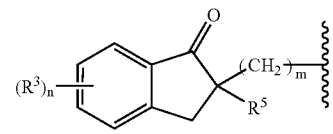

wherein the symbols have the same meanings as defined above. More preferably, mention may be made of those groups represented by the formula:

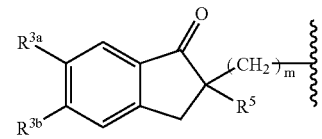

wherein $R^{3a}$, $R^{3b}$, $R^5$ and m have the same meanings as defined above. In this case, further preferred groups include those groups in which $R^{3a}$ and $R^{3b}$ represent methoxy groups. The most preferred groups in $R^1$ include a [(5,6-diemethoxy-2-chloro-1-indanon)-2-yl]methyl group, a [(5,6-diemethoxy-2-bromo-1-indanon)-2-yl]methyl group and the like.

The "$C_{3-8}$ cycloalkyl group" in the "$C_{3-8}$ cycloalkylmethyl group" represented by $R^2$ in the above formula (I) means a group having the same meaning as the $C_{3-8}$ cycloalkyl group defined above and the "$C_{3-8}$ cycloalkylmethyl group" means a group consisting of the above-mentioned "$C_{3-8}$ cycloalkyl group" and a methyl group bonded thereto, which includes, for example, cyclopropylmethyl group, cyclobutylmethyl group, cyclopentylmethyl group, cyclohexylmethyl group, cycloheptylmethyl group, cyclooctylmethyl group and the like. Among these, cyclohexylmethyl group is more preferred.

The "2,2-(alkylenedioxy)ethyl group" represented by $R^2$ above means a group (acetal group) consisting of ethyl group, the terminal carbon atom of which is substituted with a cyclic alkylenedioxy group and includes, for example, 2,2-(ethylenedioxy)ethyl group (also known as (1,3-dioxolan-2-yl)methyl group), 2,2-(propylenedioxy) ethyl group (also known as (1,3-dioxane-2-yl)methyl group) 2,2-(butylenedioxy) ethyl group (also known as (1,3-dioxepan-2-yl) methyl group) etc. Among these, 2,2-(ethylenedioxy)ethyl group is preferred.

The "aryl group" in the "aryloxy group" represented by $R^6$ above means a cyclic hydrocarbon group that constitutes an aromatic group and includes monocyclic, bicyclic or tricyclic aryl groups such as phenyl group, indenyl group, naphthyl group, azulenyl group, heptalenyl group, anthnyl group and phenanthrenyl group. The "aryloxy group" means a group consisting of the above-mentioned aryl group and oxygen atom bonded thereto and includes, for example, phenoxy group, naphthyloxy group etc.

The "aralkyloxy group" represented by $R^6$ above means a group consisting of a group having the same meaning as the aryl group and a $C_{1-6}$ alkyl group bonded thereto and the resulting aralkyl group being further bonded to oxygen atom and includes, for example, benzyloxy group, phenylethoxy group, phenylpropoxy group, naphthylmethoxy group etc.

The "halogen atom", "$C_{1-6}$ alkyl group", "$C_{3-8}$ cycloalkyl group", "$C_{1-6}$ alkoxy group", "$C_{1-6}$ alkoxyalkoxy group", "halogeno $C_{1-6}$ alkyl group", "hydroxy $C_{1-6}$ alkyl group", "cyano $C_{1-6}$ alkyl group", "halogeno $C_{1-6}$ alkoxy group", "hydroxy $C_{1-6}$ alkoxy group", "cyano $C_{1-6}$ alkoxy group", "lower acyl group", "optionally substituted amino group", "optionally substituted amide group", and "$C_{1-6}$ thioalkoxy group" have the same meanings as the halogen atom, $C_{1-6}$ alkyl group, $C_{3-8}$ cycloalkyl group, $C_{1-6}$ alkoxy group, $C_{1-6}$ alkoxyalkoxy group, halogeno $C_{1-6}$ alkyl group, hydroxy $C_{1-6}$ alkyl group, cyano $C_{1-6}$ alkyl group, halogeno $C_{1-6}$ alkoxy group, hydroxy $C_{1-6}$ alkoxy group, cyano $C_{1-6}$ alkoxy group, lower acyl group, optionally substituted amino group, optionally substituted amide group and $C_{1-6}$ thioalkoxy group as defined above, respectively. The $C_{1-6}$ alkoxycarbonyl group means a group consisting of the above-mentioned $C_{1-6}$ alkoxy group and carbonyl group bonded thereto and specifically includes, for example, methoxycarbonyl group (—$COOCH_3$), ethoxycarbonyl group (—$COOC_2H_5$) etc.

In the definition of $R^6$ above, examples of the fatty acid formed by two $R^6$ include cyclopentane ring, cyclohexane ring, cycloheptane ring, cyclooctane ring etc. Further, examples of the aromatic ring formed by two $R^6$ include benzene ring. Moreover, examples of the heterocyclic ring formed by two $R^6$ include furan ring, thiophene ring, pyrrole ring, imidazole ring, oxazole ring, thiazole ring, triazole ring, pyridine ring, pyrazine ring, pyrimidine ring, tetrahydrofuran ring, tetrahydropyran ring, dioxane ring, dioxolane ring, piperidine ring, piperazine ring, morpholine ring, thiomorpholine ring etc. Examples of the alkylenedioxy ring formed by two $R^6$ include methylenedioxy group, ethylenedioxy group, propylenedioxy group etc.

The "heterocyclic ring" represented by the ring A in $R^2$ above means a ring containing 1 to 4 hetero atoms such as nitrogen atom, sulfur atom or oxygen atom and includes a "5- to 14-membered aromatic heterocyclic ring" and a "5- to 10-membered non-aromatic heterocyclic ring". The "5- to 14-membered aromatic heterocyclic ring" includes monocyclic, bicyclic or tricyclic 5- to 14-membered aromatic heterocyclic rings containing 1 to 4 atoms selected from nitrogen atom, sulfur atom and oxygen atom, for example, (1) nitrogen-containing aromatic heterocyclic rings such as pyrrole, pyridine, pyridazine, pyrimidine, pyrazine, pyrazole, imidazole, indole, isoindole, indolizine, purine, indazole, quinoline, isoquinoline, quinolizine, phthalazine, naphthyridine, quinoxaline, quinazoline, cinnoline, pteridine, imidazotriazine, pyrazinopyridazine, acridine, phenanthridine, carbazole, carbazoline, perimidine, phenanthroline and phenazine rings; (2) sulfur-containing aromatic heterocyclic rings such as thiophene and benzothiophene rings; (3) oxygen-containing a romatic heterocyclic rings such as furan, pyran, cyclopentapyran, benzofuran and isobenzofuran rings; (4) aromatic heterocyclic rings containing 2 or more hetero atoms selected from nitrogen atom, sulfur atom and oxygen atom, such as thiazole, isothiazole, benzothiazole, benzothiadiazole, phenothiazine, isooxazole, furazane, phenoxazine, pyrazolooxazole, imidazothiazole, thienofuran, furopyrrole and pyridoxazine rings. The "5- to 10-membered non-aromatic heterocyclic ring" means a hydrocarbon ring of which 1 to 4 carbon atoms are substituted with any one of hetero atoms selected from nitrogen atom, sulfur atom and oxygen atom, it being intended to include also an unsaturated condensed ring. The "5- to 10-membered non-aromatic heterocyclic ring" includes, for example, pyrrolidine, pyrroline, piperidine, piperazine, imidazoline, pyrazolidine, imidazolidine, morpholine, tetrahydropyran, aziridine, oxirane and oxathiolane rings, phthalimide, succinimide and the like. Preferred rings in the ring A include benzene, pyridine, pyridazine, pyrimidine, pyrazine, piperidine, piperazine and morpholine rings.

In the above formula (I), a preferred example in $R^2$ includes a group represented by the formula:

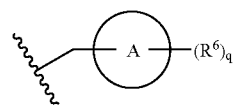

(wherein ring A, $R^6$ and q have the same meanings as defined above), and a more preferred example includes a group represented by the formula:

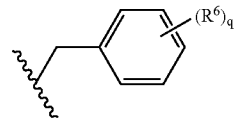

(wherein $R^6$ and q have the same meanings as defined above).

According to preferred modes of the present invention, the compound represented by the above formula (I) includes any compound selected from, for example, 1-benzyl-4-[(5,6-dimethoxy-2-chloro-1-indanon)-1-yl]methylpiperidine, 1-benzyl-4-[(5,6-dimethoxy-2-bromo-1-indanon)-2-yl]methylpiperidine, 1-benzyl-4-[(5,6-dimethoxy-2-iodo-1-indanon)-2-yl]methylpiperidine, 1-benzyl-4-[(5,6-dimethoxy-2-hydroxy-1-indanon)-2-yl]methylpiperidine, 1-benzyl-4-[(5,6-dimethoxy-2-methyl-1-indanon)-2-yl]methylpiperidine, 1-benzyl-4-[(5,6-dimethoxy-2-ethyl-1-indanon)-2-yl]methylpiperidine, 1-benzyl-4-[(5,6-dimethoxy-2-azido-1-indanon)-2-yl]methylpiperidine, 1-benzyl-4-[(5,6-dimethoxy-2-amino-1-indanon)-2-yl]methylpiperidine, 1-benzyl-4-[(5,6-dimethoxy-2-methylamino-1-indanon)-2-yl]methylpiperidine, 1-benzyl-4-[(5,6-dimethoxy-2-dimethylamino-1-indanon)-2-yl]methylpiperidine, 1-benzyl-4-[(5,6-dimethoxy-2-acetamido-1-indanon)-2-yl]methylpiperidine, 1-benzyl-4-[(5,6-dimethoxy-2-methanesulfonamido-1-indanon)-2-yl]methylpiperidine, 3-(1-benzylpiperidin-4-yl)-2-chloro-1-(2,3,4,5-tetrahydro-1H-1-benzoazepin-8-yl)-1-propanone, 3-(1-benzylpiperidin-4-yl)-2,2-dichloro-1-(2,3,4,5-tetrahydro-1H-1-benzoazepin-8-yl)-1-propanone, 5,7-dihydro-3-[(1-chloro-2-[(1-(phenylmethyl)-4-piperidinyl]ethyl]-6H-pyrrolo[4,5-f]-1,2-benzoisoxazol-6-one, 5,7-dihydro-3-[1,1-dichloro-2-[(1-(phenylmethyl)-4-piperidinyl]ethyl]-6H-pyrrolo[4,5-f]-1,2-benzoisoxazol-6-one, 1-(2-methyl-6-benzothiazolyl)-3-[1-(phenylmethyl)-4-piperidinyl]-2-chloro-1-propanone, 1-(2-methyl-6-benzothiazolyl)-3-[1-(phenylmethyl)-4-piperidinyl]-2,2-dichloro-1-propanone and the like. Of course, the present invention is not limited to the aforementioned modes.

The "pharmacologically acceptable salt" as referred to in the present invention is not particularly limited as far as it forms an addition salt together with the compound of the present invention. For example, hydrohalogenic acid salts such as hydrofluoride, hydrochloride, hydrobromide and hydroiodide; inorganic acid salts such as sulfate, nitrate, perchlorate, phosphorate, carbonate and bicarbonate; organic carboxylic acid salts, such as acetate, oxalate, maleate, tartarate and fumarate; organic sulfonic acid salts, such as methanesulfonate, trifluoromethanesulfonate, ethanesulfonate, benzenesulfonate, toluenesulfonate and camphorsulfonate; amino acid salts such as aspartate and glutamate; salts with amines such as trimethylamine salts, triethylamine salts, procaine salts, pyridine salts and phenethylbenzylamine salts; alkali metal salts such as sodium salts and potassium salts; alkaline earth metal salts such as magnesium salts and calcium salts, and hydrochloride and oxalate are preferred.

In the production of the compounds represented by the above formula (I) according to the present invention, the starting compound in the reaction may be in the form of a salt or hydrate, and is not particularly limited as far as it does not inhibit the reaction. In the case where the compounds (I) of the present invention are obtained as free forms, they can be converted into the state of salts that the compounds (I) of the present invention may form according to a conventional method. Various isomers obtained on the compound (I) of the present invention may be purified and isolated by use of common separation means (for example, recrystallization, chromatography, etc.). In particular, in the case where optically active forms of the compounds of the present invention are needed, they can be obtained, for example, by use of a method using an optically active reagent (asymmetric synthesis), a method performing optical resolution of racemic form, or the like methods.

The compounds represented by the above formula (I) according to the present invention can be formulated into agents such as tablets, powder, fine granules, granules, coated tablets, capsules, syrups, troches, inhalants, suppositories, ointments, ophthalmic ointments, ophthalmic solutions, nose drops, ear drops, poultices, lotions etc. by a common method. In the formulation, use can be made of usually used fillers, binders, lubricants, colorants, flavoring agents, and if needed, also stabilizers, emulsifiers, absorbefacients, surfactants, pH adjusting agents, preservatives, antioxidants etc. Components generally used as starting materials for medical preparations are blended and formulated by a conventional method. For example, for producing oral preparations, the compound of the present invention or a pharmacologically acceptable salt thereof and fillers, and if necessary a binder, a disintegrant, a lubricant, a colorant, a flavoring agent etc. are added and then formulated into powder, fine granules, granules, tablets, coated tablets, capsules etc. by a conventional method. Such components include, for example, animal and plant oils such as soybean oil, beef tallow and synthetic glyceride; hydrocarbons such as liquid paraffin, squalane and solid paraffin; ester oils such as octyl dodecyl myristate and isopropyl myristate; higher alcohol such as cetostearyl alcohol and behenyl alcohol; silicone resin; silicone oil; surfactants such as polyoxyethylene fatty acid esters, sorbitan fatty acid esters, glycerol fatty acid esters, polyoxyethylene sorbitan fatty acid esters, polyoxyethylene hardened castor oil and polyoxyethylene polyoxypropylene block copolymers; water-soluble polymers such as hydroxyethylcellulose, polyacrylic acid, carboxyvinyl polymer, polyethylene glycol, polyvinylpyrrolidone and methylcellulose; lower alcohols such as ethanol and isopropanol; polyhydric alcohols such as glycerol, propylene glycol, dipropylene glycol and sorbitol; sugars such as glucose and sucrose; inorganic powder such as silicic anhydride, aluminomagnesium silicate and aluminum silicate; purified water and the like. The fillers which can be used includes, for example, lactose, corn starch, white sugar, glucose, mannitol, sorbit, crystalline cellulose, silicon dioxide etc. The binder which can be used includes, for example, polyvinyl alcohol, polyvinyl ether, methylcellulose, ethylcellulose, gum arabic, tragacanth, gelatin, shellac, hydroxypropylmethylcellulose, hydroxypropylcellulose, polyvinylpyrrolidone, polypropylene glycol/polyoxyethylene block polymer, meglumine etc. The disintegrant which can be used includes, for example, starch, agar, gelatin powder, crystalline cellulose, calcium carbonate, sodium hydrogen carbonate, calcium citrate, dextrin, pectin, carboxymethylcellulose calcium and the like. The lubricant which can be used includes, for example, magnesium stearate, talc, polyethylene glycol, silica, hardened plant oil and the like. The colorant which can be used includes those of which addition to pharmaceutical preparations is permitted. The corrigent which can be used includes cocoa powder, peppermint camphor, empasm, peppermint oil, Bomeo camphor, cinnamon powder and the like. The tables and granules may of course have a glycocalyx or like coating as needed. When liquid preparations such as syrup and a preparation for injection are produced, a pH adjustor, a dissolving agent, an isotonic agent and so on and optionally a dissolution auxiliary, a stabilizer and the like as needed are added to the compound of the present invention or its pharmacologically acceptable salt, and the mixture is formulated into a preparation by a conventional method. The process for producing external preparations is not limited and a conventional method may be used for producing them. That is, the base material used upon making preparations may include various raw materials that can be usually used for drugs, quasi-drugs, cosmetics and the like. The base material which can be used specifically includes, for example, animal and plant oils, mineral oils, ester oils, waxes, higher alcohols, fatty acids, silicone oil, surfactants, phospholipids, alcohols, polyhydric alcohols, water-soluble polymers, clay minerals, purified water and the like raw materials. Further, as necessary, pH adjusting agents, antioxidant, chelating agents, antiseptical fungicidal agents, coloring agents, flavoring agents and the like may be added thereto. However, the base materials for external preparations of the present invention are not limited to these materials. Also, components having activity of differentiation, bloodstream promoting agents, germicides, antiphlogistics, cell activators, vitamins, amino acids, moisturizers, keratin solubilizers and the like components may be blended as needed. The addition amounts of the base materials are usually those amounts that will give predetermined concentrations of the components upon production of external preparations.

When administering an agent containing the compound represented by the above formula (I) according to the present invention, a salt thereof or hydrates thereof as an active ingredient, the form of the agent is not particularly limited and it may be either orally or parenterally administered by a method usually used. For example, the agent may be formulated and administered as tablets, powder, granules, capsules, syrups, troches, inhalant, suppository, injection, ointment, ophthalmic ointments, eye drops, nose drops, ear drops, poultice, lotions etc. The dosage of the pharmaceutical preparation of the present invention may be selected as appropriate depending on the severity of symptom, the age, sex, body weight, the route of the administration, the type of salt, specific kinds of the disease and so on.

The following Reference Examples, Examples (further their pharmacologically acceptable salt thereof, hydrates thereof, and a medicament or medical compositions containing them), test examples are given for illustration purposes and the compounds of the present invention should by no means be construed as being limited to the following specific examples.

REFERENCE EXAMPLE 1

1-Benzyl-4-[(5-ethoxy-6-methoxy-1-indanon)-2-yl]methylpiperidine

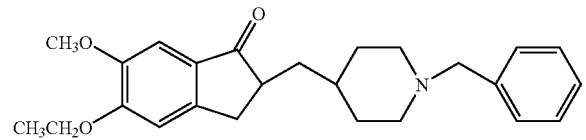

In 20 ml of THF was dissolved 0.20 g (0.55 mmol) of 1-benzyl-4-[(5-hydroxy-6-methoxy-1-indanon)-2-yl]methylpiperidine, followed by adding 0.064 ml (1.1 mmol) of ethanol, 0.29 g (1.1 mmol) of triphenylphosphine and 0.17 ml (1.1 mmol) of diethyl azodicarboxylate. After stirring at room temperature overnight, the mixture was evaporated. To the resulting residue was added 30 ml of water, followed by extrcating with 30 ml of ethyl acetate. The organic layer was washed with 30 ml of brine, dried (MgSO$_4$), and then evaporated. The resulting residue was purified by silica gel column chromatography (NH-silica gel; n-hexane/ethyl acetate), to give 0.19 g (86%) of a free form of the title compound as a pale yellow oil.

$^1$H-NMR (400 Mz: CDC$_3$) δ: 1.25–1.45 (4H, m), 1.52 (3H, t, J=7.2 Hz), 1.65–1.77 (2H, m), 1.87–1.95 (1H, m), 1.96–2.06 (2H, m), 2.65–2.73 (2H, m), 2.88–2.96 (2H, m), 3.22 (1H, dd, J=8 Hz, J=17.6 Hz), 3.54 (2H, s), 3.89 (3H, s), 4.18 (2H, q, J=7.2 Hz), 6.84 (1H, s), 7.16 (1H, s), 7.23–7.35 (5H, m).

ESI-MS: m/z=394 (M+H$^+$)

EXAMPLE 1

1-Benzyl-4-[(5,6-dimethoxy-2-chloro-1-indanon)-2-yl]methylpiperidine hydrochloride

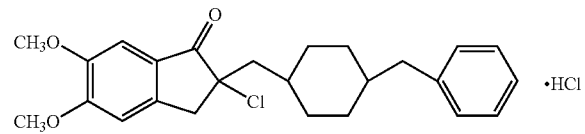

The following reaction was performed in nitrogen atmosphere.

In 10 ml of tetrahydrofuran (THF) was dissolved 0.25 g (0.66 mmol) of 1-benzyl-4-[(5,6-dimethoxy-1-indanon)-2-yl]methylpiperidine obtained in accordance with Example 4 of JP-A 1-79151. After cooling to −78° C., 0.99 ml (0.99 mmol) of a 1.0 M-lithium bis(trimethylsilyl)amide/THF solution was added therein. After elevating the temperature from −78° C. to −10° C. over 30 minutes, the solution was again cooled down to −78° C. and 0.13 g of a (0.97 mmol) N-chlorosuccinimide/THF (2 ml) solution and 0.5 ml of hexamethylphosphoramide (HMPA) were added thereto. After gradually elevating the temperature from −78° C. to room temperature and stirring for 2 hours, an aqueous saturated ammonium solution (50 ml) was added and the mixture was extracted with ethyl acetate (50 ml). The organic layer was washed with 50 ml of brine, dried (MgSO$_4$), and then evaporated. The residue was purified by NH-silica gel column chromatography (n-hexane/ethyl acetate system) and then by preparative thin layer chromatography (methylene chloride/methanol system), to give 0.17 g (62%) of a free form of the title compound as a pale yellow oil. The oil was converted into a hydrochloride by a conventional method and recrystallized from ethanol/t-butyl methyl ether, to give the title compound as pale yellow crystals.

Melting point: 202 to 204° C.

$^1$H-NMR (400 Mz: CDCl$_3$); δ(ppm) 1.66∫2.28 (7H, m), 2.60–2.74 (2H, m), 3.37–3.53 (4H, m), 3.92 (3H, s), 3.98 (3H, s), 4.13 (2H, dd, J=13.2 Hz, J=25.2 Hz), 6.80 (1H, s), 7.19 (1H, s), 7.42–7.47 (3H, m), 7.58–7.65 (2H, m), 12.42 (1H, bs).

ESI-MS; m/z 414 (M+H$^+$).

EXAMPLE 2

1-Benzyl-4-[(5,6-dimethoxy-2-bromo-1-indanon)-2-yl]methylpiperidine hydrochloride

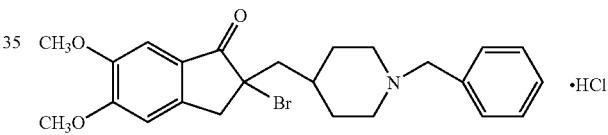

The following reaction was performed in nitrogen atmosphere.

In 10 ml of THF was dissolved 0.25 g (0.66 mmol) of 1-benzyl-4-[(5,6-dimethoxy-1-indanon)-2-yl]methylpiperidine. After cooling to −78° C., 0.99 ml (0.99 mmol) of a 1.0 M-lithium bis(trimethylsilyl)amide/THF solution was added thereto. After elevating the temperature from −78° C. to −10° C. over 30 minutes, the solution was again cooled down to −78° C. and bromine (0.051 ml, 1.00 mmol)/THF (2 ml) solution was added thereto. After gradually elevating the temperature from −78° C. to room temperature and stirring overnight, an aqueous saturated ammonium chloride solution (50 ml) was added and the mixture was extracted with ethyl acetate (50 ml). The organic layer was washed with brine (50 ml), dried (MgSO$_4$), and then evaporated. The residue was purified by NH-silica gel column chromatography (n-hexane/ethyl acetate system) and then by preparative thin layer chromatography (methylene chloride/methanol system), to give 0.071 g (24%) of a free form of the title compound as a pale yellow oil. The oil was converted into a hydrochloride by a conventional method and recrystallized from ethanol/t-butyl methyl ether, to give the titled compound as pale yellow crystals.

Melting point: 164 to 165° C.

$^1$H-NMR (400 Mz, CDCl$_3$); δ(ppm) 1.74 (1H, dd, J=6.4 Hz, J=14.8 Hz), 1.89 (1H, d, J=13.2 Hz), 2.04–2.28 (4H, m), 2.33 (1H, d, J=14.8 Hz), 2.65–2.80 (2H, m), 3.42–3.68 (4H, m), 3.92 (3H, s), 3.98 (3H, s), 4.13–4.26 (2H, m), 6.81 (1H, s), 7.22 (1H, s), 7.45 (3H, bs), 7.58–7.66 (2H, m), 12.05 (1H, bs).

ESI-MS; m/z 458 (M+H$^+$).

EXAMPLE 3

1-Benzyl-4-[(5,6-dimethoxy-2-hydroxy-1-indanon)-2-yl]methylpiperidine hydrochloride

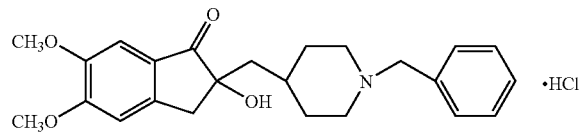

The following reaction was performed in nitrogen atmosphere.

In 10 ml of THF was dissolved (0.25 g, 0.66 mmol) of 1-benzyl-4-[(5,6-dimethoxy-1-indanon)-2-yl]methylpiperidine. After cooling to −78° C., 0.99 ml (0.99 mmol) of a 1.0 M-lithium bis(trimethylsilyl)amide/THF solution was added thereto. After elevating the temperature from −78° C. to −10° C. over 30 minutes, the solution was again cooled down to −78° C. and 0.02 g (0.96 mmol)-(10-camphorsulfonyl)oxaziridin/THF (2 ml) solution was added thereto. After gradually elevating the temperature from −78° C. to room temperature and stirring for 4 hours, an aqueous saturated ammonium chrolide solution (50 ml) was added and the mixture was extracted with ethyl acetate (50 ml). The organic layer was washed with brine (50 ml), dried (MgSO$_4$), and then evaporated. The residue was purified by NH-silica gel column chromatography (n-hexane/ethyl acetate system), to give 0.26 g (quantitative amount) of a free form of the title compound as a pale yellow oil. The oil was converted into a hydrochloride by a conventional method and solidified by using diethyl ether, to give the title compound as a pale yellow amorphous.

$^1$H-NMR (400 Mz, CDCL$_3$); δ(ppm) 1.56–2.20 (7H, m), 2.58–2.74 (2H, m), 3.06–3.50 (5H, m), 3.89 (3H, s), 3.97 (3H, s), 4.14 (2H, bs), 6.82 (1H, s), 7.11 (1H, s), 7.42 (3H, bs), 7.60 (2H, bs), 12.04 (1H, bs).

ESI-MS; m/z=396 (M+H$^+$).

EXAMPLE 4

Synthesis of 1-Benzyl-4-[(5,6-dimethoxy-2-methyl-1-indanon)-2-yl]methylpiperidine hydrochloride

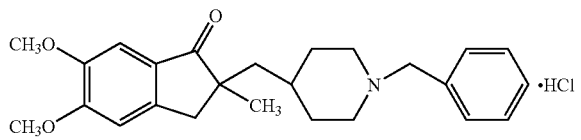

The following reaction was performed in nitrogen atmosphere.

In 10 ml of THF was dissolved 0.25 g (0.66 mmol) of 1-benzyl-4-[(5,6-dimethoxy-1-indanon)-2-yl]methylpiperidine. After cooling to −78° C., 0.99 ml (0.99 mmol) of a 1.0 M-lithium bis(trimethylsilyl)amide/THF solution was added thereto. After elevating the temperature from −78° C. to −10° C. over 30 minutes, the solution was again cooled down to −78° C. and 0.062 ml (0.99 mmol) of iodomethane was added thereto. After gradually elevating the temperature from −78° C. to room temperature and stirring for 4 hours, an aqueous saturated ammonium chrolide solution (50 ml) was added and the mixture was extracted with ethyl acetate (50 ml). The organic layer was washed with brine, dried (MgSO$_4$), and then evaporated. The residue was purified by preparative thin layer chromatography (methylene chloride/methanol system), to give 0.16 g (62%) of a free form of the title compound as a pale yellow oil. The oil was converted into a hydrochloride by a conventional method and recrystallized from ethanol/t-butyl methyl ether, to give the title compound as pale yellow crystals.

Melting point: 194 to 195° C.

$^1$H-NMR (400 Mz, CDCl$_3$); δ(ppm) 1.19 (3H, s), 1.50–1.85 (5H, m), 2.00–2.14 (2H, m), 2.44–2.60 (2H, m), 2.83 (1H, d, J=17.2 Hz), 2.99 (1H, d, J=17.2H), 3.35 (2H, bt, J=14H), 3.90 (3H, 5), 3.97 (3H, s), 4.08 (2H, bs), 6.82 (1H, bs), 7.13 (1H, s), 7.35–7.50 (3H, m), 7.58 (2H, bs), 12.25 (1H, bs).

ESI-MS; m/z=394 (M+H$^+$).

EXAMPLE 5

Synthesis of 1-Benzyl-4-[(5,6-dimethoxy-2-azido-1-indanon)-2-yl]methylpiperidine hydrochloride

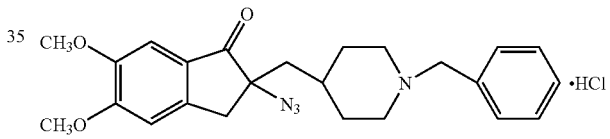

In N,N-dimethylformamide (9 ml) was dissolved 0.30 g (0.65 mmol) of 1-benzyl-4-[(5,6-dimethoxy-2-bromo-1-indanone)-2-yl]methylpiperidine obtained in Example 2, followed by adding acetic acid (3 ml) and a solution of 0.21 g (3.23 mmol) of sodium azide/water (6 ml). After stirring at 70° C. for 3 hours, the mixture was cooled down to room temperature and an aqueous saturated sodium carbonate solution (50 ml) was added. The resulting mixture was extracted with ethyl acetate (50 ml). The organic layer was washed with brine (50 ml), dried (MgSO$_4$), and then evaporated. The residue was purified by silica gel column chromatography (methylene chloride/methanol system), to give 0.18 g (65%) of a free form of the title compound as a pale yellow oil. The oil was converted into a hydrochloride by a conventional method and recrystallized from ethanol/t-butyl methyl ether, to give the title compound as pale yellow crystals.

Melting point: 153 to 154° C.

$^1$H-NMR (400 Mz, CDCl$_3$); δ(ppm) 1.64–1.74 (1H, s), 1.82–1.94 (2H, m), 1.97–2.24 (4H, m), 2.64–2.78 (2H, m), 3.01 (1H, d, J=17.2 Hz), 3.13 (1H, d, J=17.2H), 3.40–3.56 (2H, m), 3.91 (3H, s), 3.98 (3H, s), 4.20 (2H, dd, J=13.2 Hz, J=19.6 Hz), 6.82 (1H, s), 7.16 (1H, s), 7.40–7.47 (3H, m), 7.58–7.67 (2H, m).

ESI-MS; M/z=421 (M+H$^+$).

EXAMPLE 6

1-Benzyl-4-[(5,6-dimethoxy-2-chloro-1-indanon)-2-yl]methylpiperidine hydrochloride

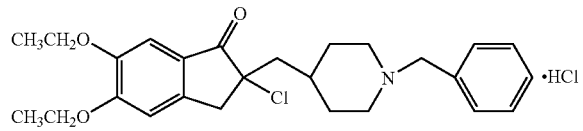

This reaction was performed in nitrogen atmosphere. In 6 ml of THF was dissolved 0.10 g (0.26 mmol) of 1-benzyl-4-[(5,6-diethoxy-1-indanon)-2-yl]methylpiperidine. After cooling to −78° C., 0.38 ml (0.38 mmol) of a 1.0 M-lithium bis(trimethylsilyl)amide/THF solution was added thereto. After elevating the temperature from −78° C. to −10° C. over 30 minutes, the solution was again cooled down to −78° C. and 4 ml of THF solution containing 0.051 g (0.38 mmol) of N-chlorosuccinimide was added thereto. After gradually elevating the temperature from −78° C. to room temperature and stirring for 4 hours, 30 ml of aqueous saturated ammonium chloride solution was added and the mixture was extracted with 30 ml of ethyl acetate. The organic layer was washed with 30 ml of brine, dried (MgSO$_4$), and then evaporated. The resulting residue was purified by preparative thin layer chromatography (methylene chloride/methanol), to give 0.058 g (51%) of a free form of the title compound as a pale yellow oil.

$^1$H-NMR (400 Mz, CDCl$_3$) δ: 1.34–1.48 (2H, m), 1.47 (3H, t, J=7.2 Hz), 1.51 (3H, t, J=7.2 Hz), 1.64–1.81 (4H, m), 1.90–2.03 (2H, m), 2.21 (1H, dd, J=4 Hz, J=14.4 Hz), 2.80–2.89 (2H, m), 3.45 (2H, s), 3.48 (2H, s), 4.11 (2H, q, J=7.2 Hz), 4.18 (2H, q, J=7.2 Hz), 6.79 (1H, s), 7.21 (1H, s), 7.22–7.33 (5H, m).

The free form was converted into hydrochloride and by a conventional method and recrystallized from ethanol/t-butyl methyl ether, to give the objective compound as pale yellow crystals.

Melting point: 166 to 167° C.
ESI-MS: m/z=442 (M+H$^+$)

EXAMPLE 7

1-Benzyl-4-[(5-ethoxy-6-methoxy-2-chloro-1-indanon)-2-yl]methylpiperidine hydrochloride

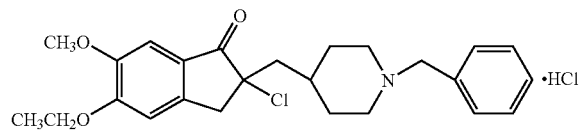

This reaction was performed in nitrogen atmosphere. In 6 ml of THF was dissolved 0.14 g (0.35 mmol) of 1-benzyl-4-[(5-ethoxy-6-methoxy-1-indanon)-2-yl]methylpiperidine obtained in Reference Example 1. After cooling to −78° C., 0.52 ml (0.52 mmol) of a solution of 1.0 M-lithium bis (trimethylsilyl)amide/THF was added. After elevating the temperature from −78° C. to −10° C. over 30 minutes, the solution was again cooled down to −78° C. and a solution of 0.070 g (0.52 mmol) of N-chlorosuccinimide in 6 ml of THF was added. After gradually elevating the temperature from −78° C. to room temperature and stirring for 4 hours, 30 ml of an aqueous saturated ammonium chloride solution was added and the resulting mixture was extracted with ethyl acetate (30 ml). The organic layer was washed with 30 ml of brine, dried (MgSO$_4$), and then evaporated. The resulting residue was purified by preparative thin layer chromatography (methylene chloride/methanol), to give 0.077 g (52%) of a free form of the title compound as a pale yellow oil.

$^1$H-NMR (400 Mz, CDCl$_3$) δ: 1.35–1.50 (2H, m) 1.53 (3H, t, J=7.2 Hz), 1.64–1.82 (4H, m), 1.92–2.04 (2H, m), 2.21 (1H, dd, J=4 Hz, J=14.4 Hz), 2.82–2.90 (2H, m), 3.46 (2H, s), 3.49 (2H, s), 3.91 (3H, s), 4.19 (2H, q, J=7.2 Hz), 6.80 (1H, s), 7.23 (1H, s), 7.24–7.33 (5H, m).

The free form was converted into a hydrochloride by a conventional method and recrystallized from ethanol/t-butyl methyl ether, to give the objective title compound as pale yellow crystals.

Melting point: 165 to 167° C.
ESI-MS: m/z 428 (M+H$^+$)

PHARMACOLOGICAL TEST EXAMPLE

Hereinafter, pharmacological test examples for demonstrating usefulness of the compounds of the present invention as medicaments will be presented.

In Vitro Acetylcholinsterase Inhibitory Effect

Using rat brain homogenate as a source of acetylcholinesterase, esterase activity was assayed in accordance with the method of Ellman et al.[1]. That is, acetylthiocholin as a substrate, a test compound and DTNB (5,5'-dithiobis(2-nitrobenzoic acid)) were added to mouse brain homogenate, and after incubation, the produced thiocholine was reacted with DTNB to produce a yellow product. This was measured as a change in absorbance at 412 nm to obtain acetylcholineesterase activity. The acetylcholineesterase inhibiting activity of each test compound was obtained as 50% inhibition concentration (IC$_{50}$). Note that the test compounds were used after dissolving them in physiological saline.
Ellman, G. L., Courtney, K. D., Andres, V. and Featherstone, R. M., (1961), Biochem. Pharmacol., 7, 88–95.

RESULTS

| Example | IC$_{50}$ (nM) |
| --- | --- |
| 1 | 2.0 |
| 6 | 2.0 |
| Donepezil Hydrochloride | 6.7 |

In the above test examples, the compounds of the present invention represented by the above formula (I), a salt thereof or hydrates thereof exhibited significant acetylcholineesterase inhibitory effect. The compounds (I) of the present invention are useful as an agent for treating, preventing or ameliorating various types of senile dementia, cerebrovascular dementia and attention deficit hyperactivity disorder, in consideration of activity, side effects, number of administration, form of administration etc. Especially, they are useful as an agent for treating, preventing or ameliorating Alzheimer-type senile dementia.

The invention claimed is:

1. A compound represented by the formula:

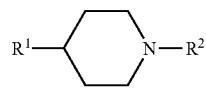
(I)

a pharmacologically acceptable salt thereof or hydrates thereof, wherein in the formula, $R^1$ represents the formula:

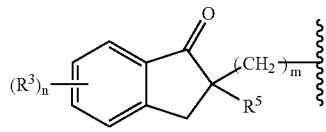

wherein:
- $(R^3)$s are the same as or different from each other and each represents hydrogen atom, a halogen atom, hydroxyl group, a $C_{1-6}$ alkyl group, a $C_{3-8}$ cycloalkyl group, a $C_{1-6}$ alkoxy group, a $C_{1-6}$ alkoxyalkoxy group, a halogeno $C_{1-6}$ alkyl group, a hydroxy $C_{1-6}$ alkyl group, a cyano $C_{1-6}$ alkyl group, an amino $C_{1-6}$ alkyl group, a halogeno $C_{1-6}$ alkoxy group, a hydroxy $C_{1-6}$ alkoxy group, a cyano $C_{1-6}$ alkoxy group, a lower acyl group, nitro group, an optionally substituted amino group, an optionally substituted carbamoyl group, mercapto group or a $C_{1-6}$ thioalkoxy group;
- $R^5$ represents a halogen atom (provided that fluorine is excluded), hydroxy group, a $C_{1-6}$ alkyl group, a $C_{1-6}$ alkoxy group, cyano group, a halogeno $C_{1-6}$ alkyl group, a cyano $C_{1-6}$ alkyl group, an amino $C_{1-6}$ alkyl group, nitro group, an azido group, an optionally substituted amino group, an optionally substituted carbamoyl group, an optionally substituted carboxyl group, mercapto group or a $C_{1-6}$ thioalkoxy group;
- m is 0 or an integer from 1 to 6; and
- n is an integer from 1 to 4; and
- $R^2$ represents a $C_{3-8}$ cycloalkylmethyl, a 2,2-(alkylenedioxy)ethyl or a group represented by the formula:

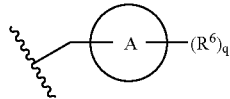

wherein:
- the ring A represents a benzene ring or a heterocyclic ring;
- $(R^6)$s are the same as or different from each other and each represents hydrogen, a halogen atom, hydroxyl group, nitrile group, a $C_{1-6}$ alkyl group, a $C_{3-8}$ cycloalkyl group, a $C_{1-6}$ alkoxy group, a $C_{1-6}$ alkoxyalkoxy group, an aryloxy group, an aralkyloxy group, a halogeno $C_{1-6}$ alkyl group, a hydroxy $C_{1-6}$ alkyl group, a cyano $C_{1-6}$ alkyl group, a halogeno $C_{1-6}$ alkoxy group, a hydroxy $C_{1-6}$ alkoxy group, a cyano $C_{1-6}$ alkoxy group, a lower acyl group, nitro group, an optionally substituted amino group, an optionally substituted amide group, mercapto group or a $C_{1-6}$ thioalkoxy group, and
- two of the $R^6$ may together form an aliphatic ring, an aromatic ring, a heterocyclic ring or an alkylenedioxy ring; and
- q is 0 or an integer from 1 to 5.

2. The compound according to claim 1, a pharmacologically acceptable salt thereof or hydrates thereof, wherein $R^1$ is represented by the formula:

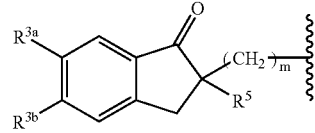

in which $R^{3a}$ and $R^{3b}$ are the same as or different from each other and each represents a $C_{1-6}$ alkoxy group;
$R^5$ represents a halogen atom (provided that fluorine is excluded), hydroxy group, a $C_{1-6}$ alkyl group, a $C_{1-6}$ alkoxy group, cyano group, a halogeno $C_{1-6}$ alkyl group, a cyano $C_{1-6}$ alkyl group, an amino $C_{1-6}$ alkyl group, nitro group, an azido group, an optionally substituted amino group, an optionally substituted carbamoyl group, an optionally substituted carboxyl group, mercapto group or a $C_{1-6}$ thioalkoxy group; and
m is 0 or an integer from 1 to 6.

3. The compound according to claim 2, a pharmacologically acceptable salt thereof or hydrates thereof, wherein $R^{3a}$ and $R^{3b}$ are methoxy groups.

4. A compound represented by the formula:

(I)

a pharmacologically acceptable salt thereof or hydrates thereof,
wherein in the formula, $R^1$ represents the formula:

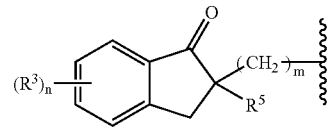

wherein:
- $(R^3)$s are the same as or different from each other and each represents hydrogen atom, a halogen atom, hydroxyl group, a $C_{1-6}$ alkyl group, a $C_{3-8}$ cycloalkyl group, a $C_{1-6}$ alkoxy group, a $C_{1-6}$ alkoxyalkoxy group, a halogeno $C_{1-6}$ alkyl group, a hydroxy $C_{1-6}$ alkyl group, a cyano $C_{1-6}$ alkyl group, an amino $C_{1-6}$ alkyl group, a halogeno $C_{1-6}$ alkoxy group, a hydroxy $C_{1-6}$ alkoxy group, a cyano $C_{1-6}$ alkoxy group, a lower acyl group, nitro group, an optionally substituted amino group, an optionally substituted carbamoyl group, mercapto group or a $C_{1-6}$ thioalkoxy group;
- $R^5$ is chlorine or bromine;
- m is 0 or an integer from 1 to 6; and
- n is an integer from 1 to 4; and
- $R^2$ represents a $C_{3-8}$ cycloalkylmethyl, a 2,2-(alkylenedioxy)ethyl or a group represented by the formula:

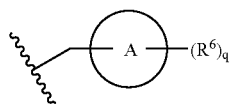

wherein:
the ring A represents a benzene ring or a heterocyclic ring;
$(R^6)$s are the same as or different from each other and each represents hydrogen, a halogen atom, hydroxyl group, nitrile group, a $C_{1-6}$ alkyl group, a $C_{3-8}$ cycloalkyl group, a $C_{1-6}$ alkoxy group, a $C_{1-6}$ alkoxyalkoxy group, an aryloxy group, an aralkyloxy group, a halogeno $C_{1-6}$ alkyl group, a hydroxy $C_{1-6}$ alkyl group, a cyano $C_{1-6}$ alkyl group, a halogeno $C_{1-6}$ alkoxy group, a hydroxy $C_{1-6}$ alkoxy group, a cyano $C_{1-6}$ alkoxy group, a lower acyl group, nitro group, an optionally substituted amino group, an optionally substituted amide group, mercapto group or a $C_{1-6}$ thioalkoxy group, and
two of the $R^6$ may together form an aliphatic ring, an aromatic ring, a heterocyclic ring or an alkylenedioxy ring; and
q is 0 or an integer from 1 to 5.

5. The compound according to claim 1, a pharmacologically acceptable salt thereof or hydrates thereof, wherein m is 1.

6. The compound according to claim 1, a pharmacologically acceptable salt thereof or hydrates thereof, wherein $R^2$ is a group represented by the formula:

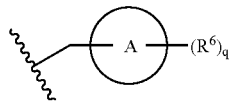

wherein:
the ring A represents a benzene ring or a heterocyclic ring;
$(R^6)$s are the same as or different from each other and each represents hydrogen, a halogen atom, hydroxyl group, nitrile group, a $C_{1-6}$ alkyl group, a $C_{3-8}$ cycloalkyl group, a $C_{1-6}$ alkoxy group, a $C_{1-6}$ alkoxyalkoxy group, an aryloxy group, an aralkyloxy group, a halogeno $C_{1-6}$ alkyl group, a hydroxy $C_{1-6}$ alkyl group, a cyano $C_{1-6}$ alkyl group, a halogeno $C_{1-6}$ alkoxy group, a hydroxy $C_{1-6}$ alkoxy group, a cyano $C_{1-6}$ alkoxy group, a lower acyl group, nitro group, an optionally substituted amino group, an optionally substituted amide group, mercapto group or a $C_{1-6}$ thioalkoxy group, and
two of the $R^6$ may together form an aliphatic ring, an aromatic ring, a heterocyclic ring or an alkylenedioxy ring; and
q is 0 or an integer from 1 to 5.

7. The compound according to claim 6, a pharmacologically acceptable salt thereof or hydrates thereof, wherein the ring A is a benzene ring.

8. A compound represented by the formula:

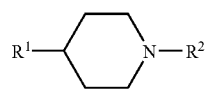

(I)

a pharmacologically acceptable salt thereof or hydrates thereof, wherein in the formula, $R^1$ represents the formula:

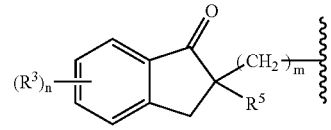

wherein:
$(R^3)$s are the same as or different from each other and each represents hydrogen atom, a halogen atom, hydroxyl group, a $C_{1-6}$ alkyl group, a $C_{3-8}$ cycloalkyl group, a $C_{1-6}$ alkoxy group, a $C_{1-6}$ alkoxyalkoxy group, a halogeno $C_{1-6}$ alkyl group, a hydroxy $C_{1-6}$ alkyl group, a cyano $C_{1-6}$ alkyl group, an amino $C_{1-6}$ alkyl group, a halogeno $C_{1-6}$ alkoxy group, a hydroxy $C_{1-6}$ alkoxy group, a cyano $C_{1-6}$ alkoxy group, a lower acyl group, nitro group, an optionally substituted amino group, an optionally substituted carbamoyl group, mercapto group or a $C_{1-6}$ thioalkoxy group;
$R^5$ represents a halogen atom (provided that fluorine is excluded), hydroxy group, a $C_{1-6}$ alkyl group, a $C_{1-6}$ alkoxy group, cyano group, a halogeno $C_{1-6}$ alkyl group, a hydroxy $C_{1-6}$ alkyl group, a cyano $C_{1-6}$ alkyl group, an amino $C_{1-6}$ alkyl group, nitro group, an azido group, an optionally substituted amino group, an optionally substituted carbamoyl group, an optionally substituted carboxyl group, mercapto group or a $C_{1-6}$ thioalkoxy group;
m is 0 or an integer from 1 to 6; and
n is an integer from 1 to 4; and
$R^2$ represents a $C_{3-8}$ cycloalkylmethyl, a 2,2-(alkylenedioxy)ethyl or a group represented by the formula:

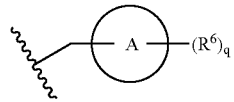

wherein the ring A is a pyridine ring;
$(R^6)$s are the same as or different from each other and each represents hydrogen, a halogen atom, hydroxyl group, nitrile group, a $C_{1-6}$ alkyl group, a $C_{3-8}$ cycloalkyl group, a $C_{1-6}$ alkoxy group, a $C_{1-6}$ alkoxyalkoxy group, an aryloxy group, an aralkyloxy group, a halogeno $C_{1-6}$ alkyl group, a hydroxy $C_{1-6}$ alkyl group, a cyano $C_{1-6}$ alkyl group, a halogeno $C_{1-6}$ alkoxy group, a hydroxy $C_{1-6}$ alkoxy group, a cyano $C_{1-6}$ alkoxy group, a lower acyl group, nitro group, an optionally substituted amino group, an optionally substituted amide group, mercapto group or a $C_{1-6}$ thioalkoxy group, and two of the $R^6$ may together form an aliphatic ring, an aromatic ring, a heterocyclic ring or an alkylenedioxy ring; and
q is 0 or an integer from 1 to 5.

9. The compound according to claim 6, a pharmacologically acceptable salt thereof or hydrates thereof, wherein q is an integer of 1 or 2.

10. The compound according to claim 1, a pharmacologically acceptable salt thereof or hydrates thereof, which is selected from the group consisting of:

1-benzyl-4-[(5,6-dimethoxy-2-chloro-1-indanon)-1-yl]methylpiperidine, 1-benzyl-4-[(5,6-dimethoxy-2-bromo-1-indanon)-2-yl]methylpiperidine, 1-benzyl-4-[(5,6-dimethoxy-2-iodo-1-indanon)-2-yl]methylpiperidine, 1-benzyl-4-[(5,6-dimethoxy-2-hydroxy-1-indanon)-2-yl]methylpiperidine, 1-benzyl-4-[(5,6-dimethoxy-2-methyl-1-indanon)-2-yl]methylpiperidine, 1-benzyl-4-[(5,6-dimethoxy-2-ethyl-1-indanon)-2-yl]methylpiperidine, 1-benzyl-4-[(5,6-dimethoxy-2-azido-1-indanon)-2-yl]methylpiperidine, 1-benzyl-4-[(5,6-dimethoxy-2-amino-1-indanon)-2-yl]methylpiperidine, 1-benzyl-4-[(5,6-dimethoxy-2-methylamino-1-indanon)-2-yl]methylpiperidine, 1-benzyl-4-[(5,6-dimethoxy-2-dimethylamino-1-indanon)-2-yl]methylpiperidine, and 1-benzyl-4-[(5,6-dimethoxy-2-acetamide-1-indanon)-2-yl]methylpiperidine.

11. The compound according to claim 1, the pharmacologically acceptable salt thereof or hydrates thereof, wherein $R^5$ in the formula represents a halogen atom (provided that fluorine is excluded), hydroxy group, a $C_{1-6}$ alkyl group, a $C_{1-6}$ alkoxy group, cyano group, a halogeno $C_{1-6}$ alkyl group, a cyano $C_{1-6}$ alkyl group, an amino $C_{1-6}$ alkyl group, nitro group, an azido group, an optionally substituted amino group, an optionally substituted carbamoyl group, mercapto group or a $C_{1-6}$ thioalkoxy group.

12. A pharmaceutical composition comprising the compound according to claim 1, a pharmacologically acceptable salt thereof or hydrates thereof; and
a pharmacologically acceptable carrier.

13. A method of treating Alzheimer-type senile dementia, said method comprising administering a pharmacologically effective amount of the compound according to claim 1, a pharmacologically acceptable salt thereof or hydrates thereof to a patient in need thereof.

14. A method of treating cerebrovascular dementia, said method comprising administering a pharmacologically effective amount of the compound according to claim 1, a pharmacologically acceptable salt thereof or hydrates thereof to a patient in need thereof.

* * * * *